United States Patent [19]

Mainusch et al.

[11] 4,297,512

[45] Oct. 27, 1981

[54] PROCESS FOR THE PREPARATION OF TRIETHYLAMINE

[75] Inventors: Klaus Mainusch; Bernhard Schleppinghoff; Klaus Munter, all of Dormagen, Fed. Rep. of Germany

[73] Assignee: EC Erdolchemie GmbH, Cologne, Fed. Rep. of Germany

[21] Appl. No.: 68,849

[22] Filed: Aug. 22, 1979

[30] Foreign Application Priority Data

Sep. 8, 1978 [DE] Fed. Rep. of Germany ....... 2839135

[51] Int. Cl.$^3$ ............................................. C07C 85/12
[52] U.S. Cl. ..................................... 564/490; 564/493
[58] Field of Search .................... 260/583 K; 564/490

[56] References Cited

U.S. PATENT DOCUMENTS 3,117,162  1/1964  Rylander et al. ............... 260/583 K
3,152,184  10/1964  Levering ..................... 260/583 K X
3,264,354  8/1966  Sawyer .......................... 260/583 K
3,673,251  6/1972  Frampton et al. ......... 260/583 K X

FOREIGN PATENT DOCUMENTS 2519838  11/1976  Fed. Rep. of Germany ... 260/583 K
1239505  7/1971  United Kingdom ........... 260/583 K Primary Examiner—John Doll
Attorney, Agent, or Firm—Sprung, Felfe, Horn, Lynch & Kramer

[57] ABSTRACT

An improved process for the preparation of triethylamine by gas phase catalytic hydrogenation of acetonitrile is disclosed, the improvement residing in employing as the catalyst a supported noble metal of Group VIII of the periodic system catalyst where the support comprises lithium aluminum spinel. The process can be carried out in the presence of up to 5% by weight of monoethylamine and/or diethylamine. The process is conducted at 80°–115° C. and under a pressure of 1 to 60 bars.

14 Claims, No Drawings

PROCESS FOR THE PREPARATION OF TRIETHYLAMINE

The present invention relates to a process for the continuous preparation of triethylamine by catalytic hydrogenation of acetonitrile in the gas phase.

In the production of acrylonitrile by the Sohio process (Ullmann's Encyklopädie der technischen Chemie (Ullmanns Encyclopaedia of Industrial Chemistry), volume 7, 4th edition, page 96, Verlag Chemie, Weinheim/Bergstraβe 1974), about 40 kg of acetonitrile are obtained, per 1 tonne of acrylonitrile, as a by-product which must be utilized economically. One of the possibilities for further processing is to convert acetonitrile into triethylamine.

Gas phase hydrogenations of acetonitrile are already known. Thus, for example, the hydrogenation of acetonitrile under a hydrogen pressure of 36 to 42 bars and at a temperature of 150° C. on a chromium/nickel catalyst is described in British Patent Specification No. 1,239,505 (Examples 1 to 3), 2.3 to 88% of monoethylamine being formed. Under 5 bars/150° C. and 230 bars/150° C. (Examples 4 and 5) 68 to 28%, respectively, of monoethylamine are obtained, in addition to diethylamine and triethylamine. The disadvantages of this process are the low liquid hourly space velocity ("LHSV") of only 0.33 volume of acetonitrile per volume of catalyst and per hour "v/v.h" (600 ml/hour of acetonitrile per 2 liters of catalyst according to Example 1–5), and the low-grade monoethylamine and diethylamine unavoidably obtained. For example, at 100% conversion, an ethylamine mixture of the following composition is obtained: 2.3% by weight of monoethylamine; 8.4% by weight of diethylamine; and 89.3% by weight of triethylamine.

Decisive disadvantages of this process are the relatively high operating pressures of 42 and 50 bars and the relatively high temperatures of 150° C., both of which favor side-reactions which reduce the selectivity. Application of such high pressures also necessitates increased investment expenditure, which has a disadvantage from the point of view of cost.

A further considerable disadvantage is to be seen in the fact that the main product triethylamine is formed with insufficient selectivity. The two by-products diethylamine and monoethylamine are present in the crude hydrogenation product to the extent of 10.7% by weight. Isolation of the triethylamine in the pure form industrially thus requires much effort and becomes considerably more expensive.

In the abovementioned patent specification, furthermore, no statements are made with regard to the lifetime of the catalysts. In fact, the process proposed therein has proved unsuitable for industrial application for economic preparation of triethylamine.

It has now been found that the abovementioned disadvantages in the continuous preparation of triethylamine by catalytic hydrogenation of acetonitrile in the gas phase can be avoided if the hydrogenation is carried out in the presence of a noble metal of group VIII of the periodic system (Mendeleev) on lithium aluminum spinel as a support. The process can be carried out in the presence of up to about 5% by weight of monoethylamine and diethylamine, relative to acetonitrile, at temperatures of 80° C. to 115° C. and under pressures of 1 to 60 bars gauge.

The supported catalyst can be employed in any desired form e.g. spheres, cylinders, extrudates, hollow strands, granules or flakes in a size of 1 to 8 mm, preferably 3 to 6 mm, diameter. The spherical form is the preferred form.

The lithium aluminum spinel support is preferably prepared from aluminum oxide with a specific surface area to 20 to 400 m$^2$/g.

The lithium aluminum catalyst support according to the invention is in itself known. Its preparation is described, for example, in German Pat. No. 1,249,255, the disclosure of which is hereby incorporated herein by reference.

Noble metal catalysts of main group VIII which may be mentioned are rhodium, palladium, iridium or platinum. The metals mentioned can be employed alone or as mixtures with one another. Vanadium and/or copper may also be added to them as a promoter. Palladium, platinum or palladium/platinum catalysts, with and without the addition of vanadium, are preferably used. Palladium/vanadium, platinum/vanadium and palladium/platinum/vanadium catalysts are particularly preferably suitable for the process according to the invention. In general, the supported catalyst contains 0.1 to 5.0% by weight, preferably 0.5 to 2.0% by weight, of the metal of group VIII of the periodic system.

If the catalyst should additionally contain vanadium as a promoter component, the vanadium content in the finished catalyst is 0.1 to 2.0% by weight, preferably 0.2 to 0.8% by weight.

The catalysts used for carrying out the process according to the invention are in themselves known. Their preparation is described, for example, in German Offenlegungsschrift No. 2,519,838, the disclosure of which is hereby specifically incorporated by reference.

The noble metal, for example palladium or platinum, is applied to the support in a known manner. For example, the noble metal, for example platinum, is applied to the support in amounts of 0.1 to 5% by weight, preferably 0.5 to 2% by weight, relative to the finished catalyst. For this purpose, the support is impregnated or sprayed, for example, with an aqueous noble metal salt solution, for example a platinum salt solution. All the commercially available noble metal compounds are suitable for the impregnation or spraying.

In general the process is carried out in the presence of 2,9 to 3,9 weight percent noble metal based upon the amount of acetonitrile.

Before reducing the noble metal compounds to the metallic form, the noble metal compounds can be converted to the noble metal hydroxide or noble metal oxide. The reduction of the noble metal compounds to the metal which usually follows can be carried out, for example, with formaldehyde and hydrazine in neutral or alkaline solution, or with formic acid, hydrogen, carbon monoxide or ethylene. However, other reducing methods can also be applied. If the catalyst should additionally contain vanadium as an active component, the vanadium can be applied to the support in the form of soluble vanadium compounds, for example vanadyl oxalate, before or after applying the main component, for example the noble metal. In general, the vanadium salt applied to the support is then converted into the oxide form by heating at temperatures of about 200° to about 500° C. The content of vanadium in the finished catalyst can be 0.1 to 2% by weight, preferably 0.2 to 0.8% by weight. Before using the catalysts thus prepared, it is appropriate to wash out wth distilled water the anions contained therein which originate from the preparation.

The catalysts mentioned, according to the invention, proved to be excellent hydrogenation catalysts, the activity and selectivity of which were unchanged, even after more than 500 operating hours.

In general, the process according to the invention can be carried out by a procedure in which hydrogen and acetonitrile and the monoethylamine are passed, in the gaseous state, through the catalyst, which is arranged in a fixed bed, in a reactor. A hydrogenation reactor of this type can be, for example, a reactor with one or more reaction tubes around which a coolant flows.

A pressure range of 1 bar gauge to 60 bars gauge, preferably 1 bar gauge to 50 bars gauge and particularly preferably 5 to 35 bars gauge, is suitable for the process according to the invention. According to the invention, the raction temperature is about 80° C. to 115° C., preferably about 85° to 110° C.

In general, amounts of about 460 to 620 ml/hour of acetonitrile are put through per 1 of catalyst in the process according to the invention. This corresponds to a liquid hourly space velocity of about 0.5 to 0.6 volume of acetonitrile per volume of catalyst and hour.

Acetonitrile of any origin and with a purity of 90% by weight to 99.9% by weight is suitable as the feed material for the hydrogenation. Acetonitrile which is obtained as a by-product in the preparation of acrylonitrile and has a purity of about 95% by weight to 99.8% by weight is preferably employed.

The hydrogenation, according to the invention, of the acetonitrile can be carried out in the presence of 0 to 5.0, preferably 0.1 to 3.0, % by weight of monoethylamine and diethylamine, relative to acetonitrile. In general, a procedure is followed here in which acetonitrile with the abovementioned degree of purity is employed in the hydrogenation and the monoethylamine and diethylamine contained in the reaction mixture in an amount of up to 5, preferably 0.1 to 3.0, % by weight after the first pass are separated off by distillation and recycled into the hydrogenation. This separating off and recycling of monoethylamine and diethylamine can be carried out continuously after starting up the hydrogenation.

The hydrogenation product can be worked up continuously or discontinuously, using methods which are in themselves known. Continuous separation of the hydrogenation mixture with isolation of pure triethylamine is preferred. For this, for example, in a downstream column, after letting down the pressure, the ammonia contained in the reaction mixture can be stripped off, or can be taken off as the top product in a pressure distillation, and put to further use. The liquid bottom product is fed to a second distillation, in which pure triethylamine is obtained in the sump or a few trays above the sump. The top product of this fractionation stage consists essentially of diethylamine and, if appropriate, unreacted acetonitrile and can be recycled again into the hydrogenation.

Summarizing the following decisive advantages can be seen in the process according to the invention: 1. By using very active and selective catalysts, the hydrogenation of acetonitrile can be carried out at surprisingly low temperatures and under surprisingly low pressures. This condition enables preparation costs to be minimal. 2. As a result of the unusually high selectivity of the catalysts according to the invention, a reaction product is obtained which consists predominantly of triethylamine and is virtually free from monoethylamine. This makes an extremely simple and cheap isolation of triethylamine in a pure form possible. 3. The catalysts to be used in the process according to the invention are distinguished by high lifetime. 4. The profitability of the acrylonitrile process is increased by the conversion of the by-product acetonitrile to triethylamine.

The Examples which follow are intended to illustrate the procedure according to the invention in more detail.

EXAMPLES 1 TO 6

The experiments were carried out in the gas phase in a V2A tube reactor 24 mm in diameter and 1.05 m in length. The reaction tube, which was filled with about 325 ml of a catalyst, was surrounded by a jacket tube, through which a heating medium or cooling medium flowed. The catalysts used consisted of lithium aluminum spinel as the support material and were prepared according to German Offenlegungsschrift No. 2,519,838. The metal dopings and specific surface areas are indicated in Table 1. 100 ml/hour of 99.0% pure acetonitrile, which was a workedup by-product of the preparation of acrylonitrile, and about 160 Nl/hour of hydrogen were pumped through the reaction tube from the top. The average reaction temperature was about 105° C. The pressure was 26 atmospheres. The reaction mixture was condensed at normal temperature. A certain proportion of the gas phase was let down as the offgas. The hydrogenation mixture, which had been freed from hydrogen and ammonia, was analyzed. The results achieved are summarised in Table 1.

| Example | Active metal of catalyst, in % by weight | Surface area $m^2/g$ | Product formed in % by weight, relative to the total amines | | |
|---|---|---|---|---|---|
| | | | Mono-amine | Di-amine | Tri-amine |
| 1 | 1.8% of Pd | 38 | <0.1 | 0.5 | 99.5 |
| 2 | 1.8% of Pt | 120 | <0.1 | 0.5 | 99.5 |
| 3 | 1.8% of Pd/0.6% of V | 23 | <0.1 | 0.4 | 99.6 |
| 4 | 1.8% of Pt/0.6% of V | 340 | 0.1 | 0.3 | 99.6 |
| 5 | 0.9% of Pd/0.9% of Pt | 290 | <0.1 | 0.5 | 99.5 |
| 6 | 0.9% of Pd/0.9% of Pt 0.6% of V | 364 | <0.1 | 0.3 | 99.7 |

The conversion was complete. The hydrogenation mixture contained virtually no monoethylamine and only traces of diethylamine. The experiments were in each case interrupted after 500 hours' running time without deactivation of the catalyst.

EXAMPLES 7 TO 9 (FOR COMPARISON)

The procedure followed was the same as in Examples 1-6, but catalysts other than the catalysts according to the invention were employed. The catalysts used and the results obtained therewith are summarized in Tables 2 and 3.

TABLE 2

| Catalysts of the Comparison Examples | | | |
|---|---|---|---|
| Catalyst | Surface area $(m^2/g)$ | Manufacturer | Designation |
| A Mo (11%)/Co (4%) on $Al_2O_3$ | 300 | BASF | M8-10 |
| B Ni (60%) on $SiO_2$ | 148 | Harshaw | Ni0104 T ⅛ |
| C Pt (0.8%) | 184 | Universal | UM 37 |

TABLE 2-continued

Catalysts of the Comparison Examples

| Catalyst | Surface area (m²/g) | Manufacturer | Designation |
|---|---|---|---|
| on SiO$_2$/Al$_2$O$_3$ | | Mathey | |

TABLE 3

Comparison of the catalysts and results

| Comparison Examples/ Catalyst | Product formed in % by weight, relative to the total amines | | | Conversion in % by weight | Comments |
|---|---|---|---|---|---|
| | Mono-amine | Di-amine | Tri-amine | | |
| 7/A | 37.2 | 48.0 | 14.8 | 16.8 | Stopped after 15 operating hours of an increase in pressure (polymers) |
| 8/B | 62.5 | 31.2 | 6.3 | 60.3 | |
| 9/C | 1.2 | 19.4 | 79.4 | 43.0 | Stopped after 20 operating hours because of too low a conversion |

The conversions of the acetonitrile were significantly lower. The experiments had to be interrupted after a very short operating time (see Table 3) because of polymerization in the reactor and/or increase in deactivation of the catalysts.

EXAMPLE 10 (FOR COMPARISON)

The procedure followed was as in Example 3, but the experiment was carried out at a reaction temperature of 150° C. An ethylamine mixture with the following constituents was formed from the acetonitrile with complete conversion (data in % by weight, relative to the total amines): 9.5% of monoethylamine, 41.0% of diethylamine and 49.5% of triethylamine.

EXAMPLE 11

The procedure followed was as in Example 3, but the experiment was carried out under a pressure of 17 atmospheres. An ethylamine mixture with the following constituents was formed from the acetonitrile with complete conversion (% by weight, relative to the total amines): <0.1% of monoethylamine, 0.4% of diethylamine and 99.6% of triethylamine.

Even after a continuous running time of 500 hours, the same values for the triethylamine selectivity were achieved.

EXAMPLE 12

The procedure followed was as in Example 1. The reaction mixture leaving the reactor was worked up continuously. In the first fractionation step, ammonia was taken off over the top under a pressure of 16 atmospheres. The bottom product stream was subjected to a second fractionation, after letting down to a pressure of 2.0 atmospheres. The bottom product stream removed contained 99.5% of triethylamine, with a total yield of 96.5% of theory. The distillate stream of this second fractionation is composed essentially of diethylamine and traces of triethylamine and is recycled into the hydrogenation. An ethylamine mixture of the following composition was obtained in the separator (% by weight, relative to the total amines): <0.1% of monoethylamine, 0.4% of diethylamine and 99.6% of triethylamine.

The conversion of acetonitrile was quantitative. The experiment was interrupted after 500 operating hours without noticeable deactivation of the catalyst.

What is claimed is:

1. In a process for the continuous preparation of triethylamine by catalytic hydrogenation of acetonitrile in the gas phase, the improvement which comprises employing as the catalyst a catalyst comprising a noble metal of Group VIII of the periodic system disposed on a lithium aluminum spinel catalyst, employing a temperature of 80° to 115° C. and a pressure of 1 to 60 bars gauge and carrying out the process in the presence of up to 3% by weight of monoethylamine and/or diethylamine relative to acetonitrile.

2. A process according to claim 1 wherein the monoethylamine and/or diethylamine are added to the reaction mixture.

3. A process according to claim 2 wherein the monoethylamine and/or diethylamine added to the reaction mixture are obtained by distillative separation from the reaction mixture of the hydrogenation.

4. A process according to claim 1 wherein acetonitrile is hydrogenated to form a reaction mixture comprising monoethylamine and diethylamine, monoethylamine and diethylamine are separated from such reaction mixture and recycled to a hydrogenation reaction mixture where they are present in a combined amount of up to 3% by weight relative to acetonitrile, the distillative separation of the monoethylamine and/or diethylamine and the recycle thereof to a hydrogenation zone being carried out continuously.

5. A process according to claim 1 wherein the hydrogenation is carried on a supported catalyst which contains 0.1 to 5% by weight of a metal of Group VIII of the periodic system.

6. A process according to claim 1 wherein the hydrogenation is carried out employing 2.9 to 3.9 weight percent of said noble metal of Group VIII based upon the amount of acetonitrile.

7. A process according to claim 1 wherein the hydrogenation is carried out in the presence of a catalyst additionally containing vanadium.

8. A process according to claim 1 wherein the hydrogenation is carried out in the presence of a catalyst which additionally contains 0.1 to 2.0% by weight vanadium.

9. A process according to claim 1 wherein the hydrogenation is carried out in the presence of a catalyst containing 0.5 to 2.0 weight percent palladium and/or platinum.

10. A process according to claim 9 wherein said catalyst additionally contains 0.2 to 0.8% by weight vanadium.

11. A process according to claim 1 wherein said lithium aluminum spinel has a specific surface area of 20 to 400 square meters per gram.

12. A process according to claim 1 wherein the hydrogenation is carried out at a temperature of 85° to 110° C. and under a pressure of 5 to 35 bars.

13. A process according to claim 1 wherein the acetonitrile which is hydrogenated is obtained as by-product in the preparation of acrylonitrile.

14. A process according to claim 1 wherein the catalyst is arranged in a fixed bed.

* * * * *